(12) United States Patent
Yabe et al.

(10) Patent No.: US 6,589,496 B1
(45) Date of Patent: Jul. 8, 2003

(54) METHOD FOR PREPARATION OF METAL OXIDE DOPED CERIUM OXIDE

(75) Inventors: Sinryo Yabe, Kita-ku (JP); Kota Tofukuji, Kita-ku (JP); Shigeyoshi Momose, Kita-ku (JP); Sakae Yoshida, Itabashi-ku (JP); Kazuyuki Tahira, Itabashi-ku (JP); Tsugio Sato, Sendai (JP)

(73) Assignee: Nippon Dewho Co., Ltd., Tokyo (JP)

( * ) Notice: Subject to any disclaimer, the term of this patent is extended or adjusted under 35 U.S.C. 154(b) by 0 days.

(21) Appl. No.: 09/867,585

(22) Filed: May 31, 2001

Related U.S. Application Data

(62) Division of application No. 09/505,730, filed on Feb. 17, 2000.

(30) Foreign Application Priority Data

May 25, 1999 (JP) .......................................... 11-144664

(51) Int. Cl.[7] ................................................. C01F 17/00
(52) U.S. Cl. ...................................... 423/263; 427/215
(58) Field of Search ........................... 423/263; 427/215

(56) References Cited

U.S. PATENT DOCUMENTS

| 4,601,755 A | * | 7/1986 | Melard et al. |
| 4,610,867 A | | 9/1986 | Seiyama et al. |

FOREIGN PATENT DOCUMENTS

| EP | 0 207 857 A | 1/1987 |
| EP | 0 517 554 A | 12/1992 |
| EP | 0 588 691 A | 3/1994 |
| EP | 0 810 181 A | 12/1997 |

OTHER PUBLICATIONS

Rajendran, M. et al., "Combustion Synthesis, Powder . . .", Journal of Materials Science, Chapman and Hall Ltd., London, GB, vol. 33, No. 20, Oct. 15, 1988, pp. 5001–5006.

* cited by examiner

*Primary Examiner*—Steven Bos
(74) *Attorney, Agent, or Firm*—Sherman & Shalloway

(57) ABSTRACT

A metal oxide doped cerium oxide has an excellent ultraviolet ray shielding effect and transparency and reduced catalytic activity. The doping mextal oxide is an oxide of a metal ion having larger ion radius than that of $Ce^{4+}$ and/or lower valence metal ion than $Ce^{4+}$, such as $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$, $Ce^{3+}$. The metal oxide doped cerium is prepared by reacting aqueous solution of cerium salt, aqueous solution of metal ion having larger ion radius than that of $Ce^{4+}$ and/or lower valence metal ion than $Ce^{4+}$ and alkali at a temperature lower than 60° C. and at pH higher than 5. An oxidizing agent may be present together with the alkali or added subsequently. Resin compositions or cosmetic compositions blended with the metal oxide doped cerium oxide have improved ultraviolet shielding effect without spoiling transparency in the visible ray region.

13 Claims, 3 Drawing Sheets

METHOD FOR PREPARATION OF METAL OXIDE DOPED CERIUM OXIDE

CROSS REFERENCE TO RELATED APPLICATION

This application is a division of copending application Ser. No. 09/505,730, filed Feb. 17, 2000, the entire disclosure of which is incorporated herein by reference, which in turn claims priority from Japanese Patent Application JP 144664/99 filed on May 25, 1999.

BACKGROUND OF THE INVENTION

1. Field of the Invention

The present invention relates to a method for the preparation of metal oxide doped cerium oxide. Further, the present invention relates to such method in which the metal oxide doped cerium oxide or a complex composed of the metal oxide solid doped cerium oxide is coated with another metal oxide or blended with a compatabilizing agent for a cosmetic composition.

2. Description of the Prior Art

As is well known, ultraviolet rays cause degradation of plastic resins, and many kinds of countermeasures are carried out to protect against such degradation. As one countermeasure method, it is widely practiced that a plastic resin is admixed with an ultraviolet shielding agent including an organic ultra-violet ray absorbing agent or an inorganic ultraviolet ray scattering agent. By admixing these agents in plastic resin, the adverse influence of ultraviolet rays is reduced. As the organic ultraviolet ray absorbing agent, salicylic acid type compound, benzophenone type compound, benzotriazole type compound or cyanoacrylate type compound can be mentioned, however, recently, the lack of heat resistance, lack of durability to weather or the safety of decomposed chemicals of these compounds are becoming serious problems. To solve these problems, fine particles of titanium dioxide or fine particles of zinc oxide, which are inorganic ultraviolet ray scattering agents, are developed, however, the lack of dispersability of these agents is a problem and the catalytic activity of these agents are becoming a new problem. Recently, especially regarding titanium dioxide, it is pointed out that the generation of singlet oxygen by its photo catalyst function is causing a new problem.

Ultraviolet rays have an adverse influence also on living bodies. Namely, it is well-known that the so called UV-B ultraviolet ray in the wavelength range of 280 to 320 nm causes cutaneous inflammations such as erythematous blister and the like while the so called UV-A ultraviolet ray in the wavelength range 320 to 400 nm causes tanning of skin by the accelerated formation of melanin. As the countermeasure method against above mentioned adverse influences of the ultraviolet rays, many kinds of sunscreen cosmetic compositions have been developed heretofore. The ultraviolet shielding agents contained in conventional sunscreen cosmetic compositions can be grossly classified into two types including an ultraviolet absorbing agent such as cinnamic acid type, benzophenone type or dibenzoylmethane type and an ultraviolet scattering agent such as zinc oxide or titanium dioxide. However, above mentioned ultraviolet absorbing agents have several problems, such as low absorptivity of ultraviolet rays and safety when the admixing amount in a cosmetic composition is too high. Further, in a case of conventional ultraviolet scattering agent, since it is impossible to improve the transparency even if the dispersibility of particles is improved, the admixing use of it not only causes the deterioration of feeling when the cosmetic composition is applied but also the skin look becomes unnatural. Recently, the use of cerium compound as an ultraviolet scattering agent has been proposed, for example, in Japanese Patent Laid Open Publication 6-145645 or Japanese Patent Laid Open Publication 7-207151. However, since cerium oxide has strong catalytic activity, it has a problem that it accelerates the oxidation decomposition of resin or oil and causes color change and generates offensive odor when admixed in cosmetic compound or resin. Thereupon, the development of new cerium compound which has a function as the ultraviolet scattering agent and does not have catalytic activity has been desired. In Japanese Patent Laid Open Publication 9-118610, silica-cerium oxide composite particle is proposed, however, the reduction of catalytic activity of the silica-cerium oxide composite particle is almost accomplished but the ability for ultraviolet ray shielding is not sufficient.

OBJECT OF THE INVENTION

The present invention addresses the above mentioned circumstance, to provide metal oxide doped cerium oxide with strong ultraviolet ray shielding ability, lower catalytic activity and with excellent transparency. Further, this invention provides a composite composition of metal oxide doped cerium oxide coated with metal oxide. Furthermore, this invention also provides a resin composition and a cosmetic composition in which the metal oxide doped cerium oxide or a composite thereof is admixed.

BRIEF SUMMARY OF THE INVENTION

The present invention provides cerium oxide doped with metal ion having larger ion radius than that of tetravalent cerium ion ($Ce^{4+}$) and/or lower valence than $Ce^{4+}$. As concrete examples of metal ions which can be used in this doping, $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$, $Ce^{3+}$ and the like can be mentioned. The desirable cerium oxide concentration in the metal oxide solid doped cerium oxide is 40 to 98 molar %. Further, when the color index of the metal oxide doped cerium oxide is estimated by L*, a* and b* values, the desirable region of L* is larger than 80, the desirable region of |a*| is smaller than 4, and desirable region of |b*| is smaller than 10. Preferably, the average particle size is ultra fine particle of 2 to 4 nanometers (nm).

Further the metal oxide doped cerium oxide of this invention can be prepared by following steps. That is, the metal oxide doped cerium oxide is formed at a temperature lower than 60° C. and at a pH higher than 5 by reacting aqueous solution of cerium salt, aqueous solution of metal ion having larger ion radius than that of $Ce^{4+}$ and/or lower valence than $Ce^{4+}$ and alkali, then by adding oxidizing agent to the reaction mixture at the temperature lower than 60° C. Furthermore the metal oxide doped cerium oxide of this invention can be prepared by adding and mixing aqueous solution of cerium salt, aqueous solution of metal ion having larger ion radius than that of $Ce^{4+}$ and/or lower valence than $Ce^{4+}$, alkali and oxidizing agent simultaneously at the temperature lower than 60° C. at a pH higher than 5.

The present invention also relates to a composite composition of the metal oxide doped cerium oxide coated by one or more kinds of oxide selected from silicon oxide, zirconium oxide, aluminum oxide, iron oxide and titanium dioxide. Further, the present invention relates to a resin composition to which the metal oxide doped cerium oxide or the composite composition thereof is blended. Still further, the present invention relates to a cosmetic composition to which the metal oxide doped cerium oxide or the composite composition thereof is blended. The surface treated metal oxide doped cerium oxide or the composite composition thereof can be blended to the cosmetic composition. The cosmetic composition can also contain an ultraviolet ray absorbing agent and/or an ultraviolet ray scattering agent. As the desirable example of the ultraviolet ray absorbing agent, one or more kinds of compound selected from oxybenzone, octyl methoxycinnamate and 4-tert-butyl-4'-methoxy dibenzoylmethane can be mentioned, and the desirable content of the ultraviolet ray absorbing agent is 0.1 to 40% by weight. As the desirable example of the ultraviolet ray scattering agent, titanium dioxide and/or zinc oxide can be mentioned, and the desirable content of the ultraviolet ray scattering agent is 0.1 to 50% by weight. Above mentioned cosmetic composition is suited to be used as a sunscreen cosmetic composition.

The metal oxide doped cerium oxide of this invention is cerium oxide doped with metal ion having larger ion radius than that of $Ce^{4+}$ and/or lower valence metal ion than $Ce^{4+}$. By doping the metal ion, the catalytic activity of cerium oxide can be reduced. Further, by doping the metal ion, the transparency of cerium oxide is improved and the ultraviolet ray shielding effect can be improved. As concrete examples of metal ion which has larger ion radius than $Ce^{4+}$ (ion radius of $Ce^{4+}$ is 0.097 nm), $Ca^{2+}$, $La^{3+}$, $Nd^{3+}$, $Eu^{3+}$, $Tb^{3+}$, $Sm^{3+}$, and $Ce^{3+}$ can be mentioned. As concrete examples of metal ion which has lower valence than $Ce^{4+}$, $Y^{3+}$, $Mg^{2+}$, $Sr^{2+}$ and $Ba^{2+}$ can be mentioned in addition to the above mentioned metal ions. These metal ions can be used alone or together. In addition, the desirable concentration of metal oxide doped cerium oxide is 40 to 98 molar %.

The metal oxide doped cerium oxide of this invention can be prepared by the following steps. That is, metal hydroxide doped cerium hydroxide is prepared, for example, at a temperature lower than 60° C. and in the condition of pH higher than 5, by reacting aqueous solution of cerium salt, aqueous solution of metal ion having larger ion radius than that of $Ce^{4+}$ and/or lower valence metal ion than $Ce^{4+}$ and alkali, then add oxidizing agent while maintaining the temperature lower than 60° C. The obtained reacted product is rinsed with water, filtered, and dried or calcined, then pulverized. Thus, the metal oxide doped cerium oxide can be obtained. As concrete examples for the preparation of the solid solution of cerium hydroxide and metal hydroxide, the following methods can be mentioned. That is, (1) adding aqueous solution of cerium salt and aqueous solution of salt of metal to be dissolved, simultaneously into a container in which alkaline solution is contained, or (2) adding aqueous solution of cerium salt, alkaline solution and aqueous solution of salt of metal to be dissolved, simultaneously into a container in which water is contained.

Furthermore, the metal oxide doped cerium oxide of this invention can be prepared by adding and mixing aqueous solution of cerium salt, aqueous solution of metal ion having larger ion radius than that of $Ce^{4+}$ and/or lower valence metal ion than $Ce^{4+}$, alkali and oxidizing agent simultaneously. For instance, at the temperature lower than 60° C. and in the condition of pH higher than 5, aqueous solution of cerium salt, aqueous solution of salt of metal to be dissolved, alkaline solution and hydrogen peroxide, which is an oxidizing agent, are added simultaneously into a container in which water is contained. The obtained reacted product is rinsed with water and filtered, dried or calcined then pulverized, thus the fine particles of metal oxide doped cerium oxide can be prepared.

Aqueous solution of cerium salt which is used in above mentioned reaction, can be prepared by dissolving, e.g. cerium carbonate, in aqueous solution of hydrochloric acid or nitric acid, or by dissolving cerium chloride, cerium nitrate, cerium sulfate or cerium acetate in water. As alkali, aqueous solution of alkali metal hydroxide, such as, sodium hydroxide or potassium hydroxide, or aqueous solution of ammonia, can be used. Further, as the salt of metal to be doped, for example, chloride, salt of nitric acid, salt of sulfuric acid or salt of acetic acid, can be mentioned. As the oxidizing agent, hydrogen peroxide, hypochlorous acid, sodium hypochlorite, potassium hypochlorite, calcium hypochlorite and ozone can be used. In above mentioned methods, the doping is carried out in aqueous solution, however, the invention is not limited to these examples.

In any kind of above mentioned reacting method, nano-size particles of metal oxide doped cerium oxide having 2 to 4 nm average diameter can be obtained by keeping the temperature of solution lower than 60° C., desirably lower than 40° C. and by maintaining pH higher than 5 during the adding process of oxidizing agent. Such kind of fine pulverized particles of metal oxide doped cerium oxide have a superior transparency in the visible ray range and have an excellent dispersability, further, have a good ultraviolet ray shielding effect.

Further, in any kind of above mentioned reacting method, the yellowish tendency of metal oxide doped cerium oxide can be moderated so that white particles are obtained. And when the color index is estimated by L*, a* and b* space, the metal oxide doped cerium oxide whose L* is larger than 80, |a*| is smaller than 4, and |b*| is smaller than 10, can be obtained. In this invention, the term of L*, a* and b* space is regulated by CIE1976L* a* b* color space which is authorized by CIE (Commission Internationale de Enluminure) in 1976. This color space is a coordinate having axis of L*, a* and b* which are regulated by following numerical formulae.

$$L^* = 116(Y/Y_0)^{1/3} - 16$$

$$a^* = 500[(X/X_0)^{1/3} - (Y/Y_0)^{1/3}]$$

$$b^* = 200[(Y/Y_0)^{1/3} - (Z/Z_0)^{1/3}]$$

(wherein, $X/X_0$, $Y/Y_0$, $Z/Z_0 > 0.008856$, X,Y and Z indicate 3 stimulate values of object color, $X_0$, $Y_0$ and $Z_0$ indicate 3 stimulate values of color source which illuminates the object, and standardized to $Y_0=100$).

In the present invention, color index estimated by L*, a* and b* space is settled to L*≧80, |a*|≦4, |b*|≦10. And each L*, a* and b* value are measured by color difference meter (product of Nihon Denshoku Kogyo).

The metal oxide doped cerium oxide of this invention can be used in the composite form, namely coated with oxide (hereinafter the composite may be referred to as "oxide coated metal oxide doped cerium oxide"). As the oxide to be used for the preparation of the oxide coated metal oxide doped cerium oxide, one or more kinds of compound selected from silicon oxide, zirconium oxide, aluminum oxide, iron oxide and titanium dioxide, may be used. By the use of composite of metal oxide doped cerium oxide which is coated with oxide, the catalytic activity can be made weaker and the dispersability can be improved.

The oxide coated metal oxide doped cerium oxide can be prepared by the further treatment of metal oxide doped cerium oxide prepared by the use of aforementioned starting materials and by aforementioned method with oxide. For example, aqueous solution of cerium salt, aqueous solution of salt of metal to be doped (e.g. salt of calcium) and aqueous solution of alkali are added into water which is kept at the temperature lower than 60° C. and higher than pH 9, then calcium hydroxide doped cerium hydroxide can be obtained. An oxidizing agent such as hydrogen peroxide is further added to generate calcium oxide doped cerium oxide. Then, the mixture is heated to a temperature higher than 80° C. while keeping pH higher than 9, aqueous solution of sodium silicate and aqueous solution of mineral acid such as hydrochloric acid, nitric acid or sulfuric acid are added to coat silicon oxide over calcium oxide doped cerium oxide, and rinsed by water, filtered, dried, calcined and pulverized. Thus, silicon oxide coated calcium oxide doped cerium oxide can be obtained. In this case, desirable amount of sodium silicate to be added is 2 to 60% by weight to coat subject of solid solution as $SiO_2$. Also in this case, by keeping pH of solution under 8 at the finishing point of oxidation, the yellowish tendency of oxide coated metal oxide doped cerium oxide can be weakened and improve the color index, and the metal oxide doped cerium oxide whose $L^*$ value is bigger than 80, absolute value of $a^*$ is smaller than 4 and absolute value of $b^*$ is smaller than 10 when color index is estimated by $L^*$ $a^*$ and $b^*$ space can be obtained. Further, by keeping pH of solution higher than 5 during oxidizing agent adding process, ultrafine particles of silicon oxide coated calcium oxide doped cerium oxide whose average particle diameter is 2 to 4 nm can be obtained.

DETAILED DESCRIPTION OF THE INVENTION

Figure 1:
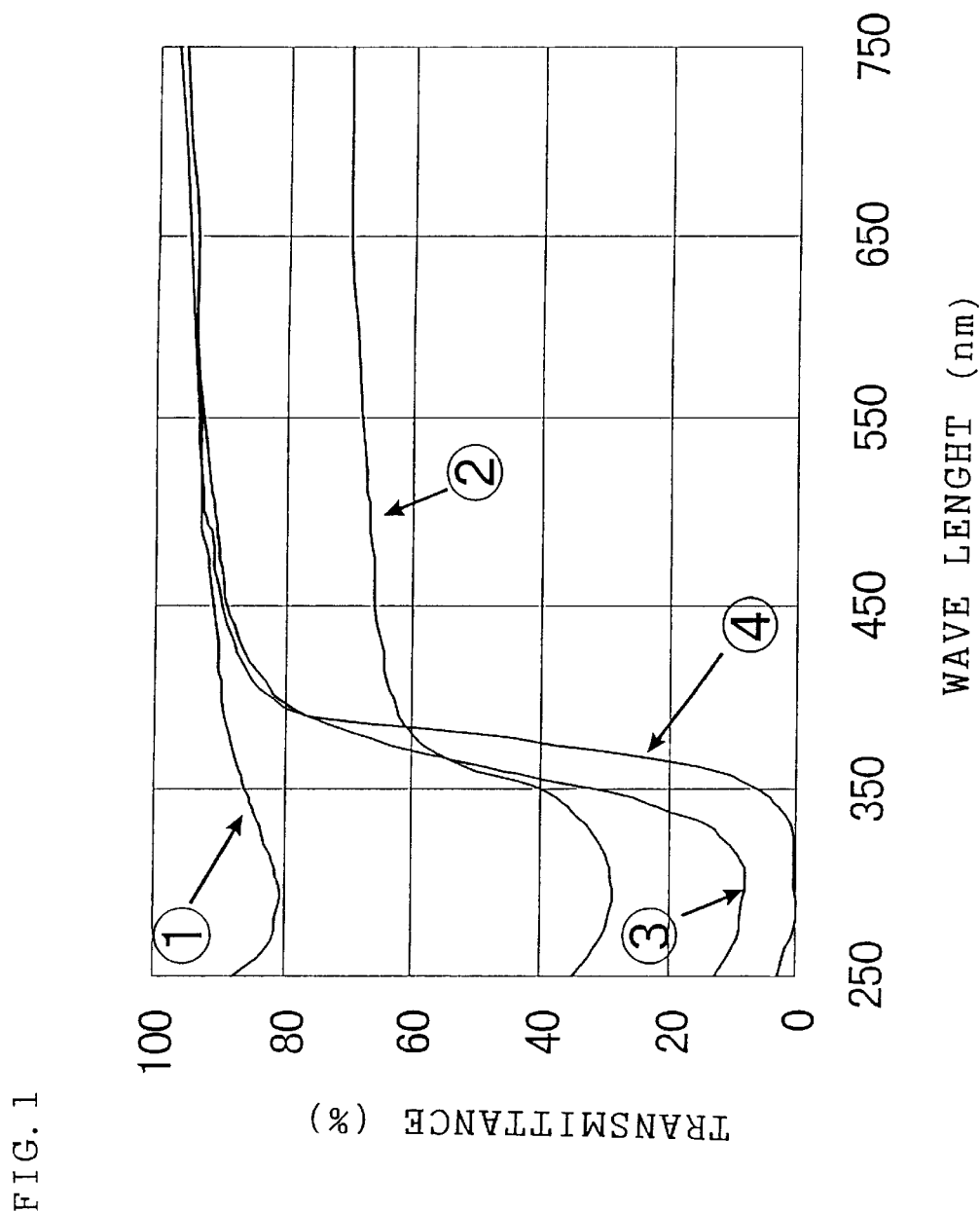
FIG. 1 is a graph which shows the light transmittance of metal oxide doped cerium oxide of this invention.

The metal oxide doped cerium oxide of this invention has an excellent ultraviolet ray shielding effect. FIG. 1 shows the results of measurement of the light transmittance as a function of wavelength of the metal oxide doped cerium oxide obtained by above mentioned method. The light transmittance is measured according to the following method. That is, each specimen is added to and dispersed in 6 ml of clear lacquer in such an amount that the content thereof is 3.0% by weight by using a Hoover muller (rotating at 50 revolutions×2) and mixed. The obtained solution is coated on a transparent quartz board to 30 μm thickness and the light transmittance is measured by a spectrophotometer (UV-2200, product of Shimadzu Seisakusho Co., Ltd.).

In FIG. 1, specimen (1) contains no additives, specimen (2) is high purity pulverized cerium oxide particles (average particle size is 10 μm) on market, specimen (3) is europium oxide doped cerium oxide of this invention whose molar ratio of $Ce^{4+}$ and $Eu^{3+}$ is 7:3, and specimen (4) is calcium oxide doped cerium oxide of this invention whose molar ratio $Ce^{4+}$ and $Ca^{2+}$ is 8:2.

As clearly understood from FIG. 1, europium oxide doped cerium oxide particles (3) and calcium oxide doped cerium oxide particles (4) of this invention are superior to high purity cerium oxide particles (2) on market in the ultraviolet ray shielding effect over the wavelength range of 250 to 400 nm, further in the transparency in the visible wavelength of 400 to 800 nm.

Figure 2:
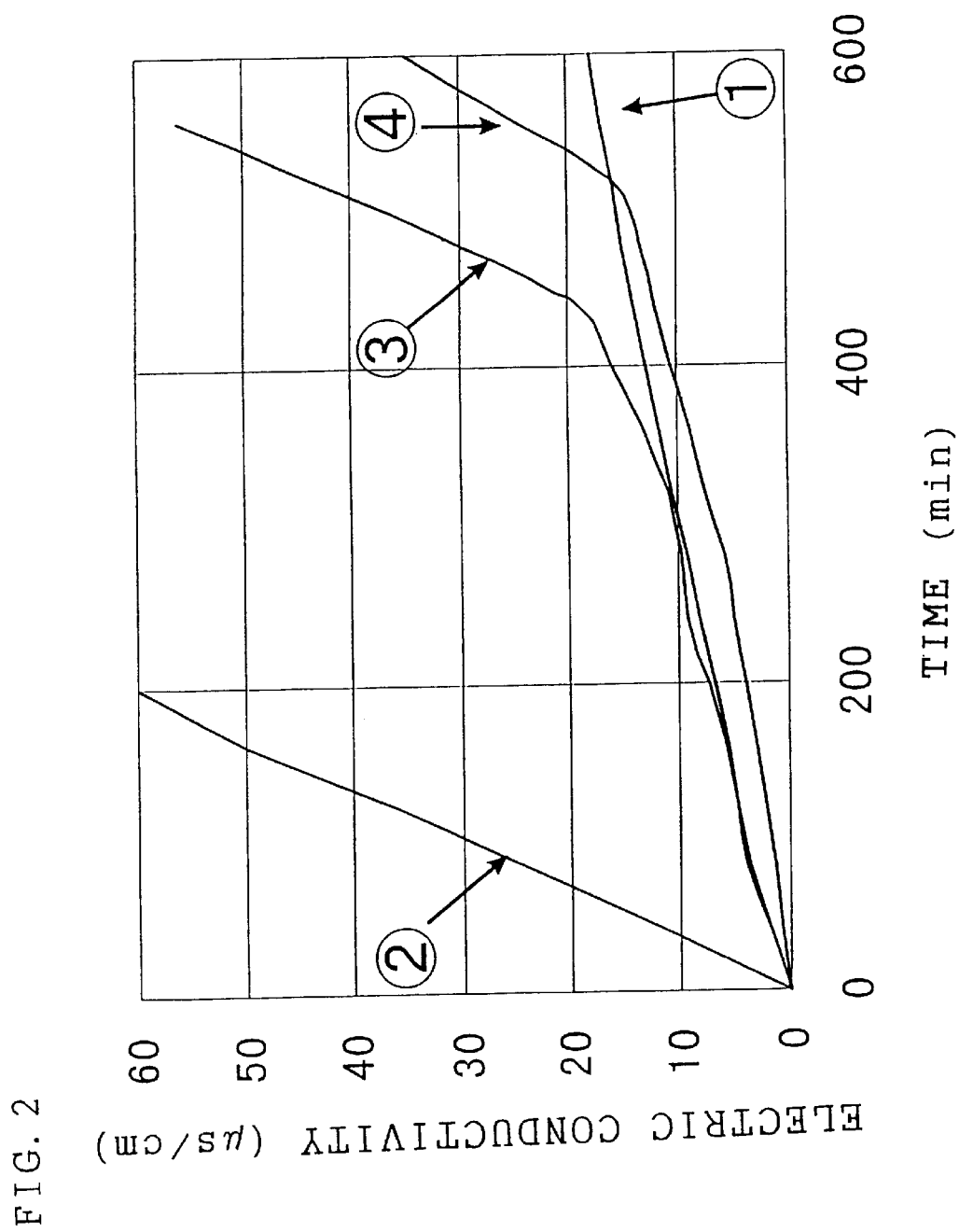
FIG. 2 is a graph which shows the catalytic activity of metal oxide doped cerium oxide of this invention.

FIG. 2 shows the estimation results of catalytic activity of metal oxide doped cerium oxide obtained by above mentioned method measured by RANSHIMAT method which is a kind of CDM (Contactometric Determination Method). As the CDM apparatus, Model E679 (product of Metrom Co.) is used, 0.5 g of specimen and 5 g of caster oil (product of Ito Seiyu Co.) are mixed together, poured into a sealed container placed in a thermostat set up to 130° C. for 10 hours. Air is introduced with bubbling by 20 liter/hour flow rate to the caster oil. Air of head space is introduced to the water contained in a separated flask, and the change of electroconductivity of trapped water caused by volatile decomposition of caster oil is detected by measuring cell. The degree of change of electric conductivity with lapse of time is regarded as the intensity of catalytic activity. The same specimen used at the measurement of light transmittance is used.

As clearly understood from FIG. 2, the europium oxide doped cerium oxide particles (3) and the calcium oxide doped cerium oxide particles (4) of this invention have smaller tendency to promote the oxidation and decomposition of caster oil compared with the high purity cerium oxide particles (2) on market, and it is obvious that the catalytic activity of (3) and (4) is remarkably reduced.

A resin composition and a cosmetic composition of this invention are illustrated as follows. In general, a resin composition degrades by the absorption of ultraviolet rays of sun light. As the countermeasure method against the degradation by ultraviolet rays, the metal oxide doped cerium oxide is blended to the resin composition. Thus, the resistance to light is improved and the decomposition by light can be prevented or reduced. Further, the light decomposition of the contents which is covered by a transparent resin composition by ultraviolet ray can be prevented or reduced. When the catalytic activity of metal oxide doped cerium oxide of this invention is compared with that of cerium oxide, it is remarkably weaker, therefore, the oxidizing decomposition of resin composition caused by cerium oxide can be reduced. The resin composition of this invention indicates a molded product of synthetic resin such as polyvinylchloride, polypropylene, polyethylene, polyamide, polyester or polycarbonate, or natural resin, or a coating in which the resins are blended.

A cosmetic composition of this invention is illustrated as follows. The cosmetic composition of this invention exhibits excellent transparency and high sunscreening effect by virtue of the inventive metal oxide doped cerium oxide particles contained therein. Because the catalytic activity of the metal oxide doped cerium oxide of this invention is remarkably weaker than that of cerium oxide, the decomposition of blended component in cosmetic compound such as oil caused by cerium oxide can be reduced. As a concrete example of the formulation type of the inventive cosmetic composition, a skin care cosmetic composition such as milk lotion, skin lotion and the like, a make up cosmetic composition such as foundation or lipstick and a hair care cosmetic composition can be mentioned, desirably a sunscreening cosmetic composition can be mentioned. The amount of the metal oxide doped cerium oxide to be blended in a cosmetic composition is not limited, however, the desirable amount is 1 to 70% by weight.

Optionally, the metal oxide doped cerium oxide or oxide coated metal oxide doped cerium oxide composite particles are subjected to a surface treatment before being introduced into a cosmetic composition. As the concrete example for the surface treatment method, a treatment by ordinary type oil and fat, a metal soap, silicone, dialkyl phosphoric acid, perfluoroalkyl group containing compound, amino acid, lecithin or collagen can be mentioned.

The sunscreening effect exhibited by the inventive cosmetic composition can be further enhanced by including in the composition other well known ultraviolet ray absorbers and/or ultraviolet ray scattering agents in combination with the metal oxide doped cerium oxide particles. The ultraviolet ray absorbing agent suitable for the purpose includes oxybenzone, octyl methoxycinnamate, 4-tert-butyl-4'-methoxydibenzoylmethane and the like either singly or as a combination of two kinds or more according to need. The containing amount thereof, though not particularly limited, is usually in the range from 0.1 to 40% by weight of the composition. The ultraviolet ray scattering agent used for the above mentioned purpose is preferably a fine powder of titanium dioxide or zinc oxide, more preferably, having an average particle diameter not exceeding 0.05 $\mu$m. The containing amount thereof is desirably in the range of from 0.1 to 50% by weight.

Any conventional cosmetic ingredients can be used together with the cosmetic compositions. Typical examples of such ingredients are cosmetic powder, surface active agents, oil, polymeric compounds, aesthetic ingredients, moisturizing agents, coloring agents, preservatives, perfumery and so on each in a limited amount not to decrease the advantages obtained by the invention.

The effect of this invention is illustrated as follows. The catalytic activity of metal oxide doped cerium oxide of this invention is reduced by doping metal oxide in cerium oxide, the transparency in the visible range is good and the effect to shield the ultraviolet ray at A-range and the ultraviolet ray at B-range is increased. And, the resin composition or the cosmetic composition in which the metal oxide doped cerium oxide particles are blended have an excellent transparency and ultraviolet ray shielding effect. A resin or a cosmetic in which conventional cerium oxide is blended has a tendency that the contained oil or blended components are easily oxidized and decomposed by the catalytic activity of contained cerium oxide. On the contrary, since the catalytic activity of metal oxide doped cerium oxide of this invention is reduced, such defect can not be observed and has an excellent stability for aging. A complex of metal oxide doped cerium oxide whose surface is coated with oxide, can further reduce and weaken the catalytic activity and can improve the dispersability.

EXAMPLES

The present invention will be understood more readily with reference to the Examples and the Comparative Examples, however, these are only intended to illustrate the invention and not be construed to limit the scope of the invention.

Example 1
Europium Oxide Doped Cerium Oxide Particles 342 g of cerium chloride ($CeCl_3$) is dissolved in water and 3 liter of cerium chloride aqueous solution is prepared. 155 g of europium chloride ($EuCl_3$) is dissolved in water and 3 liter of europium chloride aqueous solution is prepared. Further 237 g of sodium hydroxide (NaOH) is dissolved in water and 12 liter of sodium hydroxide aqueous solution is prepared. Furthermore, 118 g of 30wt % hydrogen peroxide is dissolved in water and 3 liter of hydrogen peroxide aqueous solution is prepared. 12 liter of sodium hydroxide aqueous solution is heated to 30–40° C. and the cerium chloride aqueous solution and europium chloride aqueous solution are added simultaneously under constant stirring while maintaining pH of reacting solution higher than 11 and temperature of the solution lower than 40° C. After adding, stirring is continued for 30 minutes, while maintaining the temperature of reacting solution at 60° C., then aqueous solution of hydrogen peroxide is added. After the adding, constant stirring is continued for 30 minutes, then the reacted product is rinsed by water, filtered and dried. Europium oxide doped cerium oxide particles whose molar ratio of $Ce^{4+}$ and $Eu^{3+}$ is 7:3 is obtained.

Example 2
White Colored Calcium Oxide Doped Cerium Oxide Particles 390 g of cerium chloride ($CeCl_3$) is dissolved in water and 3 liter of cerium chloride aqueous solution is prepared. 45 g of calcium chloride ($CaCl_2$) is dissolved in water and 3 liter of aqueous solution of calcium chloride is prepared. Further, 237 g of sodium hydroxide (NaOH) is dissolved in water and 8 liter of sodium hydroxide aqueous solution is prepared. Furthermore, 118 g of 30 wt % hydrogen peroxide is dissolved in water and 3 liter of hydrogen peroxide aqueous solution is prepared. To 8 liter of water heated to 30–40° C., the cerium chloride aqueous solution, calcium chloride aqueous solution and sodium hydroxide aqueous solution are added simultaneously with constant stirring while maintaining pH of reacting solution at 9 to 11 and temperature of the solution lower than 40° C. After the reaction, hydrochloric acid is added to adjust pH of reacting solution to 5 to 7 and the temperature of solution to 60° C., and the aqueous solution of hydrogen peroxide is added. The reacted product is rinsed with water, filtered and dried. Calcium oxide doped cerium oxide particles whose molar ratio of $Ce^{4+}$ and $Ca^{2+}$ is 8:2 is obtained.

The color index of obtained solid solution is L* value=94.0, a* value=–1.6 and b* value=6.2.

20 g of obtained powder is press molded on a pan of 6 cm and L*, a* and b* values are measured by a color difference meter (product of Nihon Denshoku Kogyo).

Example 3
Ultrafine Particles of Calcium Oxide Doped Cerium Oxide 390 g of cerium chloride ($CeCl_3$) is dissolved in water and 3 liter of cerium chloride aqueous solution is prepared. 45 g of calcium chloride ($CaCl_2$) is dissolved in water and 3 liter of aqueous solution of calcium chloride is prepared. Further 237 g of sodium hydroxide (NaOH) is dissolved in water and 3 liter of sodium hydroxide aqueous solution is prepared. Furthermore, 118 g of 30 wt % hydrogen peroxide is dissolved in water and 3 liter of hydrogen peroxide aqueous solution is prepared. To 8 liter of water heated to 30–40° C., cerium chloride aqueous solution, calcium chloride aqueous solution and sodium hydroxide aqueous solution are added simultaneously by constant stirring, while maintaining pH of reacting solution 9 to 11 and temperature of the solution lower than 40° C. After the reaction, the reacted product is rinsed with water, filtered and dried, thus the calcium oxide doped cerium oxide whose molar ratio of $Ce^{4+}$ and $Ca^{2+}$ is 8:2 is obtained.

The average particle diameter of metal oxide is 2.8 nm. The particle diameter is measured by a transmission electron microscope (product of JEOL Co., Ltd.). Namely, diameter of 100 particles are measured by naked eyes of inspector and averaged.

Example 4
Composite of Silicon Oxide Coated Calcium Oxide Doped Cerium Oxide 562 g of sodium silicate solution (content of $SiO_2$ is 28.5 wt %) is dissolved in water and 2 liter of sodium silicate solution is prepared. 75.8 g of 95 wt % sulfuric acid is diluted with water and 2 liter of diluted sulfuric acid is prepared. The aqueous solution containing calcium oxide doped cerium oxide obtained in Example 2 is heated to a temperature higher than 80° C. with constant stirring, aqueous solution of sodium silicate and diluted sulfuric acid are added simultaneously as to maintain pH of reacting solution higher than 9. After the adding of both solutions, the resulting solution is further stirred for another 30 minutes and pH of reacting solution is adjusted to 7 to 8 by adding dilute sulfuric acid. The reacted product is rinsed with water, filtered, dried and pulverized, thus 30 wt % $SiO_2$ coated calcium oxide doped cerium oxide (silicon oxide coated calcium oxide doped cerium oxide) is obtained.

Example 5

Figure 3:
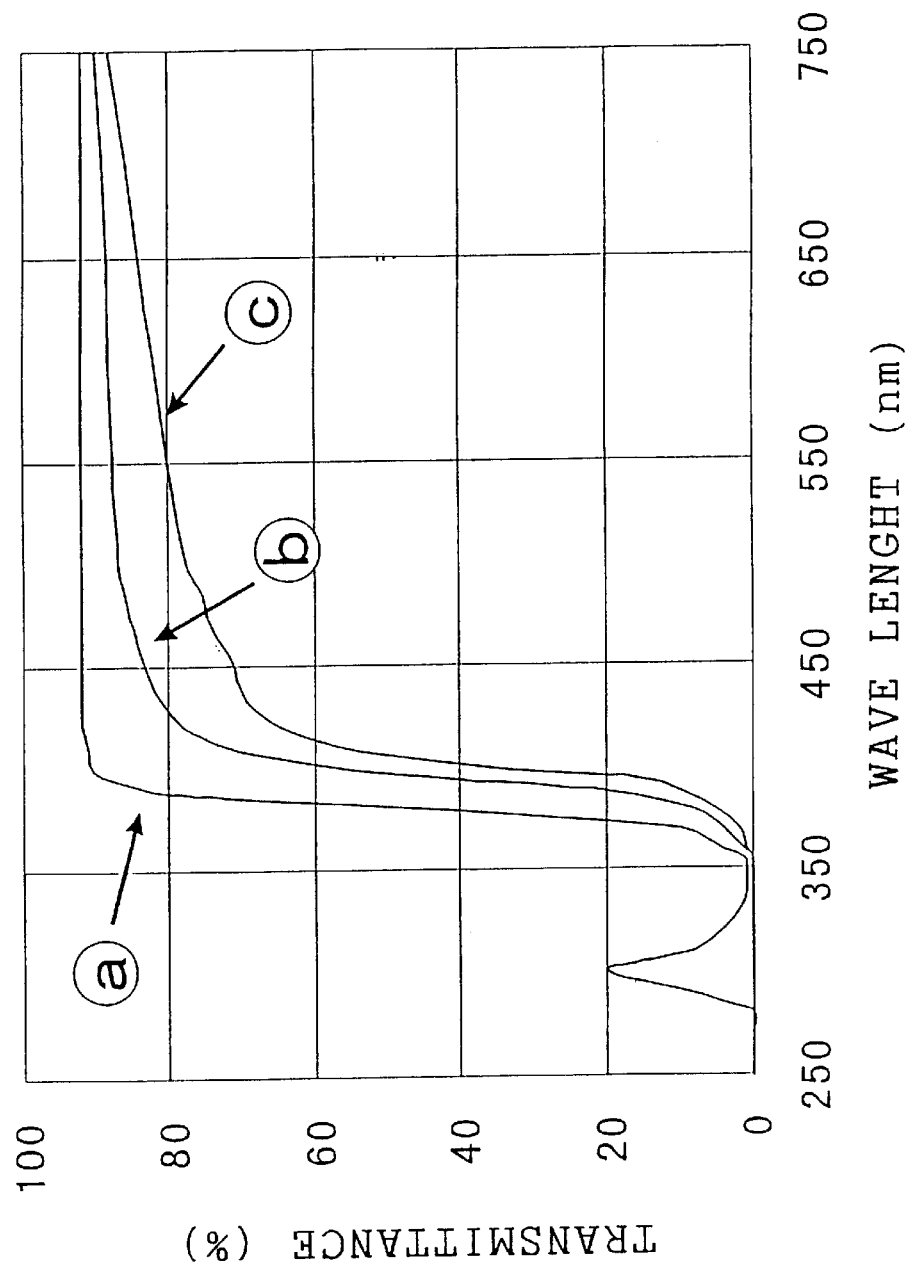
FIG. 3 is a graph which shows the light transmittance of the polyvinyl chloride sheet containing the metal oxide doped cerium oxide of this invention.

0.05 and 1 wt % of the white calcium oxide doped cerium oxide particles obtained in Example 2 are blended to plasticized polyvinyl chloride resin. The polyvinyl chloride resin without doped particles and the two resin compositions blended with both amounts of particles are each shaped into a sheet having a thickness of 0.24 mm by using hot calendering rollers. Each of thus prepared sheets are subjected to the measurement of the transmittance on a spectrophotometer (UV-2200, product of Shimadzu Seisakusho Co., Ltd.). Results illustrated in FIG. 3 are obtained.

Specimen a is a sheet with no additives,

Specimen b is a sheet containing 0.5 wt % of calcium oxide doped cerium oxide.

Specimen c is a sheet containing 1.0 wt % of calcium oxide doped cerium oxide.

It is clearly understood from FIG. 3, that the calcium oxide doped cerium oxide of this invention can improve the shielding effect in the range of ultraviolet rays by the higher blending ratio, however it maintains good transparency in the range of visible rays.

Example 6

Four kinds of cream foundation of following recipe are prepared containing metal oxide doped cerium oxide or composite of silicon oxide coated calcium oxide doped cerium oxide obtained from Example 1 to Example 4.

Recipe

|  | wt % |
|---|---|
| (1) stearic acid | 5.0 |
| (2) oleophilic glyceryl monostearate | 2.5 |
| (3) cetanol | 1.5 |
| (4) isopropylene glycol monolaurate | 2.5 |
| (5) liquid parafin | 8.0 |
| (6) isopropyl myristate | 7.0 |
| (7) propyl paraben | 0.1 |
| (8) purified water | 47.3 |
| (9) triethanolamine | 1.2 |
| (10) sorbitol | 3.0 |
| (11) methyl paraben | 0.2 |
| (12) titanium dioxide | 8.0 |
| (13) kaolin | 5.0 |
| (14) doped particles obtained from Example 1, 2, 3 or 4 | 3.0 |
| (15) bentonite | 1.0 |
| (16) red iron oxide | 2.5 |
| (17) yellow iron oxide | 2.0 |
| (18) black iron oxide | 0.2 |

Method for Preparation (a) Ingredients (12) to (14) and (16) to (18) are blended together.

(b) Ingredient (15) is admixed with (8), heated at 80° C. to effect full swelling, then ingredients (9) to (11) are added and dissolved therein. To the mixture, the prepared mixture (a) is added and dissolved at 80° C. (water phase).

(c) Ingredients (1) to (7) are mixed together and dissolved at 80° C. (oily phase).

(d) To the prepared (water phase), the prepared (oily phase) is added and emulsified. After that, the emulsion is cooled down to 35° C. under constant stirring.

The cream foundations obtained as above, exhibit excellent transparency of coated layer along with good spreadability and an excellent sunscreening effect.

Example 7

150 g of the ultrafine particles of calcium oxide doped cerium oxide obtained in Example 3 and 200 g of purified water are taken into a flask and are mixed together with heating to 70° C. to prepare an aqueous slurry. Further, an aqueous emulsion obtained from 6 g of diethanolamine salt of perfluoroalkyl phosphoric acid ester (Asahiguard AG 530, a product of Asahi Glass Co., Ltd.) and 150 g of purified water are admixed and emulsified. The obtained emulsion is added gradually into the slurry and followed by continuous stirring for 1 hour. After acidification, the aqueous dispersion is rinsed with water, filtered, dried to yield 154 g of fluorinated calcium oxide doped cerium oxide fine particles (hereinafter shortened to fluorinated doped particle).

Example 8

150 g of the white calcium oxide doped cerium oxide obtained in Example 2 and 200 g of isopropanol are taken into a flask and are mixed together with heating to 70° C. to prepare an aqueous slurry, then 3 g of methyl hydrogen polysiloxan (product of Shin-Etsu Chemical Co., Ltd.) is added and mixed for 1 hour. Isopropyl alcohol is removed from the mixture by heating and vacuuming to give 152 g of silicone treated white calcium oxide doped cerium oxide (hereinafter, shortened to silicone treated doped particles).

Example 9

A sunscreen milk lotion is prepared by using fluorinated doped particles obtained in Example 7 according to the following recipe and preparing method.

Recipe

|  | wt % |
|---|---|
| (1) fluorinated doped particles | 10.0 |
| (2) microcrystalline wax | 1.0 |
| (3) beeswax | 2.0 |
| (4) squalane | 10.0 |
| (5) dimethicone (10 cSt) | 10.0 |
| (6) decamethyl cyclopentasiloxane | 10.0 |
| (7) sorbitan sesquioleate | 4.0 |
| (8) polyoxyethylene-methylpolysiloxane copolymer | 1.0 |
| (9) oxybenzone | 0.1 |
| (10) 1,3-butyleneglycol | 9.0 |
| (11) preservative | q.s. |
| (12) purified water | balance |
| (13) perfume | q.s. |

Method for Preparation (a) Ingredients (2) to (9) are melted together by heat, and ingredient (1) is added and heated to 70° C.

(b) Ingredients (10) to (12) are mixed together by heating up to 70° C., and obtained mixture is added to (a) and emulsified.

(c) After (b) is cooled down, ingredient (13) is added and mixed, thus the sunscreen milk lotion is obtained.

Comparative Example 1

A sunscreen milk lotion is prepared by same recipe and same method as Example 9 except using high purity cerium oxide particles (average particle size is 10 μm) on the market instead of ingredient (1).

When the sunscreen milk lotion of Comparative Example 1 is applied on human skin, it exhibits a pale-white color and white powderiness which does not give a natural feeling of cosmetic finish. On the contrary, the sunscreen milk lotion of Example 9 which relates to this invention exhibits a transparent and good cosmetic finish along with an excellent sunscreen effect and preservability.

Example 10

A powder foundation is prepared by using silicone treated solid doped particles obtained in Example 8 according to the following recipe and preparing method.

Recipe

|  | wt % |
|---|---|
| (1) silicone treated talc | 20.0 |
| (2) silicone treated mica | balance |
| (3) silicone treated titanium dioxide | 12.0 |
| (4) silicone treated red iron oxide | 1.0 |
| (5) silicone treated yellow iron oxide | 3.0 |
| (6) silicone treated black iron oxide | 3.0 |
| (7) silicone treated doped particles | 20.0 |
| (8) silicone treated zinc oxide | 1.0 |
| (9) squalane | 5.0 |
| (10) glyceryl tri-2-ethylhexanoate | 2.0 |
| (11) white vaseline | 1.0 |
| (12) preservative | q.s. |
| (13) perfume | q.s. |

Method for Preparation
(a) Ingredients (1) to (8) are blended together by a Henschel mixer.
(b) Ingredients (9) to (11) are heated and blended together and ingredients (12) and (13) are added.
(c) The obtained mixture in (b) is pulverized into a powder, molded by pressing and a powder foundation is obtained.

Comparative Example 2

A powder foundation is prepared by same recipe and same method as Example 10 except using high purity cerium oxide particles (average particle size is 10 μm) on the market instead of ingredient (7).

When the powder foundation of Comparative Example 2 is applied on human skin, it exhibits a pale-white color and white powderiness which does not give a natural feeling of cosmetic finish. On the contrary, the powder foundation of Example 10 which relates to this invention exhibits a transparent and good cosmetic finish along with an excellent sunscreen effect and preservability.

Example 11

A lipstick is prepared by using fine particles of calcium oxide doped cerium oxide obtained in Example 3 according to the following recipe and preparing method.

Recipe

|  | wt % |
|---|---|
| (1) ethylene-propylene copolymer | 9.0 |
| (2) microcrystalline wax | 5.0 |
| (3) candelilla wax | 3.0 |
| (4) ceresin wax | 3.0 |
| (5) lanolin | 10.0 |
| (6) caster oil | 20.0 |
| (7) hexyldecyl 2-ethylhexanoate | 26.9 |
| (8) D & C Red No. 6 | 2.0 |
| (9) D & C Red No. 7 | 1.0 |
| (10) D & C Orange No. 5 | 0.1 |
| (11) fine particles of calcium oxide doped cerium oxide | 20.0 |

Method for Preparation
(a) Ingredients (8) to (11) are blended together and added to a part of ingredient (6), then are mixed and dispersed by a mixing roller.
(b) Ingredients (1) to (5), remaining part of the ingredient (6) and (7) are heated and blended together, then prepared (a) is added and further mixed homogeneously.
(c) A container for lipstick is filled with the molten mixture of (b) and cooled down rapidly, thus a lipstick is obtained.

Comparative Example 3

A lipstick is prepared by same recipe and same method as Example 11 except using fine particles of titanium dioxide instead of ingredient (11).

When the lipstick of Comparative Example 3 is applied on human lips, it exhibits a pale-white color and does not give a natural and healthy feeling on lip. On the contrary, the lipstick of Example 11 which relates to this invention exhibits transparency with healthy coloration along with an excellent sunscreen effect and preservability.

Example 12

A pressed powder is prepared by using europium oxide doped cerium oxide obtained in Example 1 according to the following recipe and preparing method.

Recipe

|  | wt % |
|---|---|
| (1) europium oxide doped cerium oxide | 50.0 |
| (2) talc | 30.0 |
| (3) sericite | 6.0 |
| (4) kaolin | balance |
| (5) titanium dioxide | 3.0 |
| (6) zinc myristate | 2.0 |
| (7) red iron oxide | 0.2 |
| (8) yellow iron oxide | 0.8 |
| (9) squalane | 2.0 |
| (10) octyl methoxycinnamate | 2.0 |
| (11) preservative | q.s. |
| (12) perfume | q.s. |

Method for Preparation
(a) Ingredients (1) to (8) are blended together.
(b) Ingredients (9) to (12) are blended together and added to (a) and mixed homogeneously.
(c) The obtained mixture (b) is pulverized into a powder, molded by pressing and a pressed powder is obtained.

Comparative Example 4

A pressed powder is prepared by same recipe and same method as Example 12 except using fine particles of titanium dioxide instead of ingredient (1).

When the pressed powder of Comparative Example 4 is applied on human skin, it exhibits a pale-white color and white powderiness which does not give a natural feeling of cosmetic finish. On the contrary, the pressed powder of Example 12 which relates to this invention exhibits transparency and good cosmetic finish along with an excellent sunscreen effect and preservability.

What is claimed is:

1. A method for producing a metal oxide doped cerium oxide consisting essentially of the steps of:

reacting, at a temperature lower than 60° C., and at a pH higher than 5,
   (a) aqueous solution comprising cerium salt,
   (b) aqueous solution of metal ion having (i) a larger ion radius than that of tetravalent cerium ion, or (ii) lower valence than that of tetravalent cerium ion, or (iii) both larger ion radius and lower valence than that of tetravalent cerium ion, and
   (c) alkali, and adding
   (d) an oxidizing agent to said reaction mixture at a temperature below 60° C.,
   wherein said cerium oxide is doped with a metal having at least one of lower valence or larger ion radius, than tetravalent cerium ion.

2. A method for producing a metal oxide doped cerium oxide consisting essentially of, mixing and reacting, at a temperature lower than 60° C., and at a pH higher than 5,
   (a) aqueous solution comprising cerium salt,
   (b) aqueous solution of metal ion having (i) a larger ion radius than that of tetravalent cerium ion, or (ii) lower valence than that of tetravalent cerium ion, or (iii) both larger ion radius and lower valence than that of tetravalent cerium ion,
   (c) alkali, and
   (d) oxidizing agent,
   wherein said cerium oxide is doped with a metal having at least one of lower valence or larger ion radius, than tetravalent cerium ion.

3. The method according to claim 1 or claim 2, wherein said metal ion is at least one metal ion selected from the group consisting of $Ca^{2+}$, $Y^{3+}$, $La^{3+}$, $Nd^{3+}$, $Eu^{3+}$, $Tb^{3+}$, $Sm^{3+}$, $Mg^{2+}$, $Sr^{2+}$, $Ba^{2+}$, and $Ce^{3+}$.

4. The method according to claim 1 or claim 2, wherein said metal oxide doped cerium oxide has a color index, estimated by values of L*, a* and b*, wherein $L^*\geq 80$, $|a^*|\leq 4$, and $|b^*|\leq 10$.

5. The method according to claim 1 or claim 2, wherein the metal oxide doped cerium is characterized by an average particle size of from 2 to 4 nanometers.

6. The method according to claim 1 or claim 2, wherein said reacting is carried out at a temperature below 40° C.

7. The method according to claim 6, wherein said reaction in the presence of said oxidizing agent is carried out at a pH higher than 9.

8. A method for producing a metal oxide doped cerium oxide comprising the steps of:

reacting, at a temperature lower than 60° C., and at a pH higher than 5,
   (a) aqueous solution comprising cerium salt,
   (b) aqueous solution of metal ion having (i) a larger ion radius than that of tetravalent cerium ion, or (ii) lower valence than that of tetravalent cerium ion, or (iii) both larger ion radius and lower valence than that of tetravalent cerium ion, and
   (c) alkali, and adding
   (d) an oxidizing agent to said reaction mixture at a temperature below 60° C.,
   wherein said cerium oxide is doped with a metal having at least one of lower valence or larger ion radius, than tetravalent cerium ion, and
   coating said metal oxide doped cerium oxide with at least one metal oxide selected from the group consisting of silicon oxide, zirconium oxide, aluminum oxide, iron oxide and titanium dioxide.

9. The method according to claim 8, wherein said metal ion is at least one metal ion selected from the group consisting of $Ca^{2+}$, $Y^{3+}$, $La^{3+}$, $Nd^{3+}$, $Eu^{3+}$, $Tb^{3+}$, $Sm^{3+}$, $Mg^{3+}$, $Sr^{2+}$, $Ba^{2+}$, and $Ce^{3+}$.

10. The method according to claim 8, wherein said metal oxide doped cerium oxide has a color index, estimated by values of L*, a* and b*, wherein $L^*\geq 80$, $|a^*|\leq 4$, and $|b^*|\leq 10$.

11. The method according to claim 8, wherein the metal oxide doped cerium is characterized by a particle size of from 2 to 4 nanometers.

12. The method according to claim 8, wherein said reacting is carried out at a temperature below 40° C.

13. The method according to claim 12, wherein said reaction in the presence of said oxidizing agent is carried out at a pH higher than 9.

* * * * *

UNITED STATES PATENT AND TRADEMARK OFFICE
CERTIFICATE OF CORRECTION

PATENT NO.     : 6,589,496 B1
DATED          : July 8, 2003
INVENTOR(S)    : Sinryo Yabe et al.

It is certified that error appears in the above-identified patent and that said Letters Patent is hereby corrected as shown below:

<u>Title page,</u>
Item [73], change "[73] Assignee: Nippon Dewho Co., Ltd." to
-- [73] Assignee: Nippon Denko Co., Ltd. --

Signed and Sealed this

Seventh Day of October, 2003

JAMES E. ROGAN
*Director of the United States Patent and Trademark Office*